US012651337B2

(12) United States Patent　　　　(10) Patent No.:　US 12,651,337 B2
Jayaraman et al.　　　　　　　　　　(45) Date of Patent:　　Jun. 9, 2026

(54) ARTIFICIAL INTELLIGENCE (AI) BASED METHOD AND SYSTEM FOR ANALYZING A WOUND

(71) Applicant: Tata Consultancy Services Limited, Mumbai (IN)

(72) Inventors: Srinivasan Jayaraman, Milford, OH (US); Anandakrishnan Kizhakke Changoth, Kochi (IN); Shreyamsha Kumar Bidare Kantharajappa, Kokata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 357 days.

(21) Appl. No.: 18/455,429

(22) Filed: Aug. 24, 2023

(65) Prior Publication Data

US 2024/0087116 A1　　Mar. 14, 2024

(30) Foreign Application Priority Data

Sep. 14, 2022　(IN) ............................. 202221052530

(51) Int. Cl.
　　G06T 7/00　　　　(2017.01)
　　B29C 64/393　　　(2017.01)
　　　　　　　(Continued)
(52) U.S. Cl.
　　CPC .......... G06T 7/0012 (2013.01); B29C 64/393 (2017.08); G06T 7/11 (2017.01);
　　　　　　　(Continued)
(58) Field of Classification Search
　　CPC ..... G06T 7/0012; G06T 7/11; G06T 2200/24; G06T 2207/20036; G06T 2207/20081;
　　　　　　　(Continued)

(56) References Cited

U.S. PATENT DOCUMENTS

2015/0140058 A1*　5/2015　Tumey .................. C12M 41/48
　　　　　　　　　　　　　　　　　425/375
2016/0328855 A1*　11/2016　Lay .......................... G06T 7/11
　　　　　　　　　　(Continued)

FOREIGN PATENT DOCUMENTS

CN　　　　106164929 B　　2/2021
JP　　　　2022513486 A　　2/2022

OTHER PUBLICATIONS

Chen et al. NPL "Encoder-Decoder with Atrous Separable Convolution for Semantic Image Segmentation" (Year: 2018).*
　　　　　　　(Continued)

*Primary Examiner* — Andrew W Bee
*Assistant Examiner* — Winta Gebreslassie
(74) *Attorney, Agent, or Firm* — Finnegan, Henderson, Farabow, Garrett & Dunner, LLP

(57)　　　　　　ABSTRACT

Monitoring the progression of a wound is critical, as it involves repeated clinical trips and lab tests over days. An artificial intelligence (AI) based system and method for analyzing wounds on a person is provided. The system is configured to take an image of the wound taken from a camera of a person. This image is then provided to the physician after the analysis and physician is able to provide a feedback to the person in terms of a healing index. In the analysis part, the system provides a fully automatized wound segmentation and quantify the parameters that assist wound care professionals. An AI based estimation module is provided, implemented with morphological operations, connected component analysis, and shape analysis, improving accuracy and providing the wound parameter and metrics such as area, perimeter, circle diameter, major and minor axis length of an ellipse.

20 Claims, 7 Drawing Sheets

(51) Int. Cl.
| | |
|---|---|
| *G06T 7/11* | (2017.01) |
| *G16H 30/40* | (2018.01) |
| *G16H 50/20* | (2018.01) |

(52) U.S. Cl.
CPC ............. *G16H 30/40* (2018.01); *G16H 50/20* (2018.01); *G06T 2200/24* (2013.01); *G06T 2207/20036* (2013.01); *G06T 2207/20081* (2013.01)

(58) Field of Classification Search
CPC ...... B29C 64/393; G16H 50/20; G16H 30/40; G06N 3/096; G06V 10/26; G06V 10/20; G06V 10/32; G06V 10/40; G06V 10/70
See application file for complete search history.

(56) References Cited

U.S. PATENT DOCUMENTS

| | | | |
|---|---|---|---|
| 2021/0201479 A1* | 7/2021 | Fan | G16H 30/40 |
| 2021/0295528 A1* | 9/2021 | Fuchs | G06V 10/751 |
| 2023/0081305 A1* | 3/2023 | Islam | G06T 3/40 |
| | | | 382/128 |

OTHER PUBLICATIONS

Ferreira et al. NPL "Experimental Study on Wound Area Measurement with Mobile Devices" (Year: 2021).*
Anisuzzaman, D.M. et al., "Image Based Artificial Intelligence in Wound Assessment: A Systematic Review", Date: 2021, Publisher: arxiv, Link: https://arxiv.org/ftp/arxiv/papers/2009/2009.07141.pdf.
Buis, Lorraine, "Fully Automated Wound Tissue Segmentation Using Deep Learning on Mobile Devices: Cohort Study", Title of the item: JMIR Mhealth Uhealth, Date: 2022, vol. 10; Issue: 4, Link: https://www.ncbi.nlm.nih.gov/pmc/articles/PMC9077502/?report=printable.
Scebba, Gaetano et al., "Detect-and-segment: A deep learning approach to automate wound image segmentation", Title of the item: Informatics in Medicine Unlocked, Date: 2022, vol. 29, Publisher: Elsevier, Link: https://www.sciencedirect.com/science/article/pii/S2352914822000375.
Wang, Chuanbo et al., "Fully automatic wound segmentation with deep convolutional neural networks", Title of the item: Scientific Reports, Date: 2020, Publisher: Nature, Link: https://www.nature.com/articles/s41598-020-78799-w.pdf.
Patel, Yash, "Deep Learning-Based Object Detection in Wound Images", Date: May 2020, Publisher: University of Wisconsin—Milwaukee, Link: https://dc.uwm.edu/cgi/viewcontent.cgi?article=3419&context=etd.
Zoppo, Gianluca et al., "AI technology for remote clinical assessment and monitoring", Title of the item: Journal of Wound Care, Date: 2020, vol. 29; Issue: 12, Publisher: JWC, Link: https://www.magonlinelibrary.com/doi/pdf/10.12988/jowc.2020.29.12.692.
Chinoa, Daniel Y.T. et al., "Segmenting skin ulcers and measuring the wound area using deep convolutional networks", Title of the item: Computer Methods and Programs in Biomedicine, Date: 2020, vol. 191, Publisher: Elsevier, Link: https://www.sciencedirect.com/science/article/pii/S016926071931404X.
Wagh, Ameya et al., "Semantic Segmentation of Smartphone Wound Images: Comparative Analysis of AHRF and CNN-Based Approaches", Title of the item: IEEE Access, Date: 2020, Link: https://www.ncbi.nim.nih.gov/pmc/articles/PMC7695230/.
Anisuzzaman, D.M. et al., "A Mobile App for Wound Localization Using Deep Learning", Title of the item: IEEE Access, Date: 2022, Link: https://ieeexplore.ieee.org/stamp/stamp.jsp?arnumber=9785640.

* cited by examiner

100

Patient's Portal

Health Care Provider

Physician's or Health Care works Portal

Wound Image

ARTIFICIAL INTELLIGENCE (AI) BASED METHOD AND SYSTEM FOR ANALYZING A WOUND

PRIORITY CLAIM

This U.S. patent application claims priority under 35 U.S.C. § 119 to: India Application No. 202221052530, filed on Sep. 14, 2022. The entire contents of the aforementioned application are incorporated herein by reference.

TECHNICAL FIELD

The disclosure herein generally relates to the field of wound management, and, more particularly, to an artificial intelligence (AI) method and system for analyzing a wound of a person.

BACKGROUND

Millions of patients around the world suffering from acute and chronic nonhealing wounds, which cause a great reduction in quality of life in those patients. These wounds require periodic examination and thorough treatment to prevent deterioration. Otherwise, they can lead to severe complications such as limb amputations and death. Monitoring the progression of the wound is critical, as it involves repeated clinical trips and lab tests over days. Chronic wounds take around a 3-month period, which require continuous monitoring. Further, chronic wounds fail to progress through the phases of healing in an orderly and timely manner thereby requiring hospitalization and additional treatment that adds billions in cost for health care services annually. This healing time duration is unpredicted, as it depends on various factors such as etiology, age, nutrition, comorbidity condition of patient, medication, and environments.

The cost of healthcare services for all the wounds are estimated to be around $96.8B in United States alone. This has led to the development of wound management system that has become an essential part of the chronic wound treatment.

Wound measurement is one of the important components in the wound management system, the accuracy of which influences the diagnosis and treatment by the healthcare professionals. Also, it is critical to the evaluation of wound healing trajectory and to determine the future treatment for the patients by the doctors. In addition, the wound area gives an effective and reliable index of later complete wound healing. The most healthcare professionals depend only on imprecise manual measurement and optical assessment of wounds, which is time-consuming and often inaccurate causing negative impact on patients such as infection risks, inaccurate measurements, and discomfort to patients. These problems can be solved by exploiting image processing and computer vision techniques paired with artificial intelligence (AI). Evaluation of wound images using image processing and AI is a challenging task due to the complexities involved in the wound capturing process such as variable lighting condition, time constraints in clinical laboratories.

SUMMARY

Embodiments of the present disclosure present technological improvements as solutions to one or more of the above-mentioned technical problems recognized by the inventors in conventional systems. For example, in one embodiment, a system for analyzing a wound is provided.

The system comprises a user interface, one or more hardware processors and a memory. The user interface receives a plurality of images of a plurality of wounds as an input. The memory is in communication with the one or more hardware processors, wherein the one or more first hardware processors are configured to execute programmed instructions stored the memory, the memory further comprises: a training module configured to train a deep learning model using the plurality of preprocessed images, wherein the deep learning model having an encoder decoder architecture, the encoder decoder architecture comprises: a pre-trained Resnet50 as the encoder, an Atrous spatial pyramid pooling (ASPP) comprising of dilated convolution, wherein the ASPP is connected to the encoder, a bilinear up sampler configured to up sample the plurality of images by a factor of four, and a channel wise attention mechanism using squeeze and excitation (SE) network, designed to improve representational power of the network by enabling to perform dynamic channel-wise feature recalibration; an image segmentation module configured to: preprocess an input image of the wound to be analyzed; generate an output image from preprocessed image using the trained deep learning model; and post-process the output image using a binary segmentation mask with a fixed threshold of a predefined number; an AI based estimation module configured to: perform morphology operations on the segmented image to remove small regions and spurious noises to fill small holes within the wound to improve a true positive rate; perform connected component analysis on the binary image to label connected regions; calculate a plurality of wound parameters of the wound by measuring the labelled connected regions; and overlay the calculated plurality of wound parameters and wound segmented boundary on the image of the wound.

In another aspect, a method for analyzing a wound is provided. Initially, a plurality of images of a plurality of wounds is received as an input. The plurality of images then preprocessed. In the next step, a deep learning model is trained using the plurality of preprocessed images, wherein the deep learning model having an encoder decoder architecture, the encoder decoder architecture comprises: a pre-trained Resnet50 as the encoder, an Atrous spatial pyramid pooling (ASPP) comprising of dilated convolution, wherein the ASPP is connected to the encoder, a bilinear up sampler configured to up sample the plurality of images by a factor of four, and a channel wise attention mechanism using a squeeze and excitation (SE) network, designed to improve representational power of the SE network by enabling to perform dynamic channel-wise feature recalibration. In the next step, an image of the wound to be analyzed is provided. The image is then preprocessed. In the next step, an output image is generated from preprocessed image using the trained deep learning model. Further, the output image is post-processed using a binary segmentation mask with a fixed threshold of a predefined number to get a segmented output image. In the next step, morphology operations are performed on the segmented output image to remove small regions and spurious noises to fill small holes within the wound to improve a true positive rate. Further, connected component analysis is performed on the morphology operated image to label connected region. In the next step, a plurality of wound parameters of the wound is calculated by measuring the labelled connected regions. And finally, the calculated plurality of wound parameters and the wound segmentation boundary or region is overlaid on the image of the wound for user/physician's diagnosis.

In yet another aspect, one or more non-transitory machine-readable information storage mediums comprising one or more instructions which when executed by one or more hardware processors cause analyzing a wound. Initially, a plurality of images of a plurality of wounds is received as an input. The plurality of images then preprocessed. In the next step, a deep learning model is trained using the plurality of preprocessed images, wherein the deep learning model having an encoder decoder architecture, the encoder decoder architecture comprises: a pre-trained Resnet50 as the encoder, an Atrous spatial pyramid pooling (ASPP) comprising of dilated convolution, wherein the ASPP is connected to the encoder, a bilinear up sampler configured to up sample the plurality of images by a factor of four, and a channel wise attention mechanism using a squeeze and excitation (SE) network, designed to improve representational power of the SE network by enabling to perform dynamic channel-wise feature recalibration. In the next step, an image of the wound to be analyzed is provided. The image is then preprocessed. In the next step, an output image is generated from preprocessed image using the trained deep learning model. Further, the output image is post-processed using a binary segmentation mask with a fixed threshold of a predefined number to get a segmented output image. In the next step, morphology operations are performed on the segmented output image to remove small regions and spurious noises to fill small holes within the wound to improve a true positive rate. Further, connected component analysis is performed on the morphology operated image to label connected region. In the next step, a plurality of wound parameters of the wound is calculated by measuring the labelled connected regions. And finally, the calculated plurality of wound parameters and wound segmented boundary is overlaid on the image of the wound.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
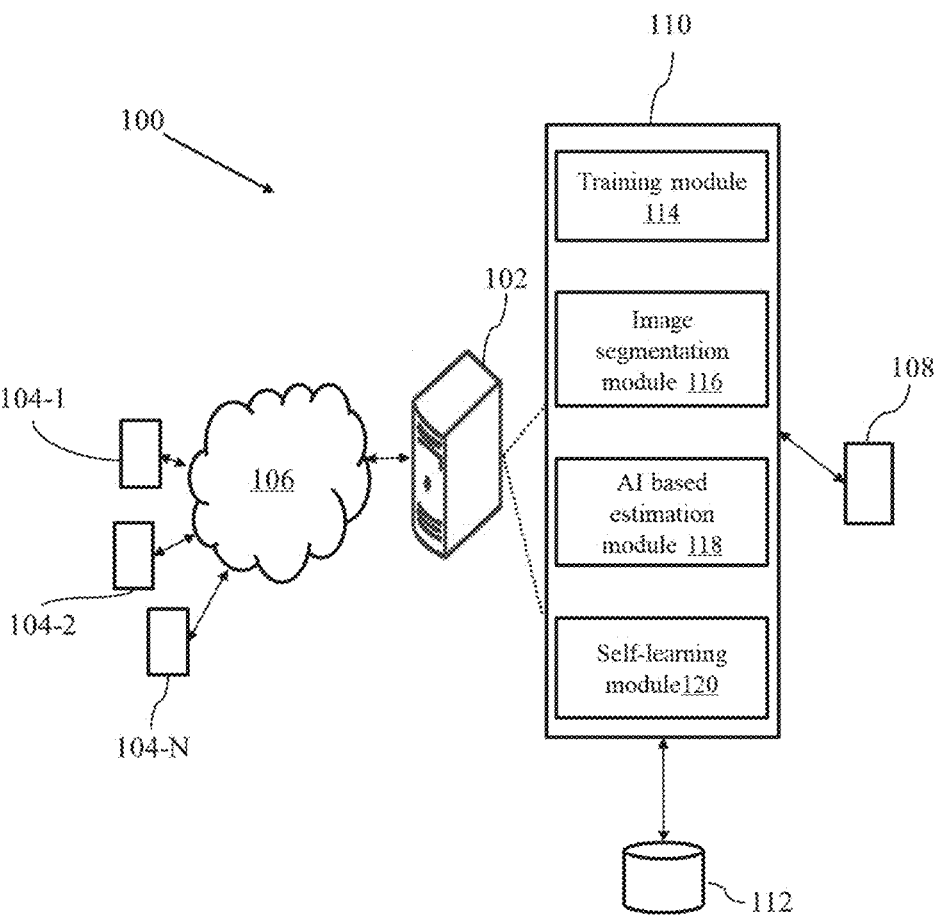
FIG. 1 shows a block diagram of an artificial intelligence (AI) based system for analyzing a wound according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Monitoring the progression of a wound is critical, as it involves repeated clinical trips and lab tests over days. Chronic wounds take around a 3-month period, which require continuous monitoring. This has led to the development of wound management system that has become an essential part of the chronic wound treatment.

Wound measurement is one of the important components in the wound management system, the accuracy of which influences the diagnosis and treatment by the healthcare professionals. Also, it is critical to the evaluation of wound healing trajectory and to determine the future treatment for the patients by the doctors.

In the prior art, the wound management system comprises wound segmentation. The wound segmentation has been roughly categorized into traditional image processing and deep learning-based methods. The former category focuses on combining image processing techniques with machine learning approaches by using hand-crafted features for processing wound images. Most of these methods suffer from one or more of the following limitations: (a) no guarantee of optimal result as they depend on manually curated parameters and empirically handcrafted features, (b) the hand-crafted features are affected by illumination, image resolution and skin pigmentation, (c) they are not immune to severe pathologies and rare cases that are very impractical from a clinical perspective. The latter category focuses on the exploitation of deep learning (DL) networks on wound segmentation. Unlike with the traditional machine learning and image processing-based methods, which make decisions based on the handcrafted features, the DL based-methods combine both feature extraction and decision making.

The present disclosure provides an artificial intelligence (AI) based system and method for analyzing wounds on a person. The system is configured to take an image of the wound taken from a camera of a person. In addition, the AI module estimate the healing index based on the wound parameter for example using the area of wound history. This image is then provided to the physician after the analysis and physician is able to provide feedback to the person in terms of a healing index. In the analysis part, the system provides a fully automatized wound segmentation and quantify the parameters that assist wound care professionals. An AI based estimation module is provided, implemented with morphological operations, connected component analysis, and shape analysis, improving accuracy and providing the wound parameter and metrics such as area, perimeter, circle diameter, major and minor axis length of an ellipse.

Referring now to the drawings, and more particularly to FIG. 1 through FIG. 6B, where similar reference characters denote corresponding features consistently throughout the figures, there are shown preferred embodiments and these embodiments are described in the context of the following exemplary system and/or method.

Figure 2:
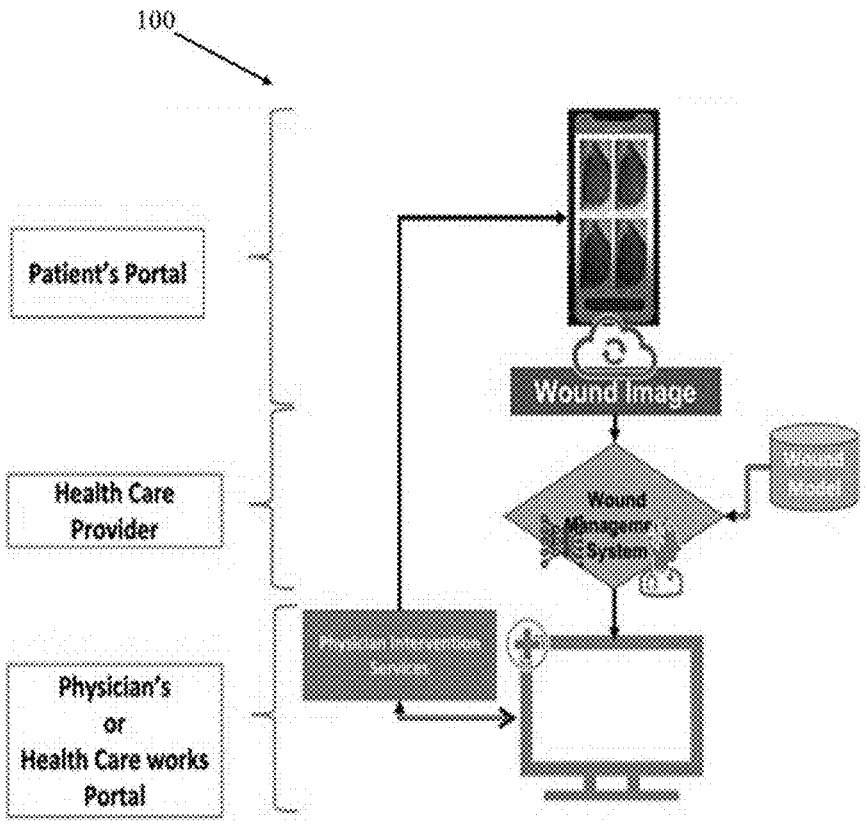
FIG. 2 shows an architecture of the system of FIG. 1 for analyzing the wound according to some embodiments of the present disclosure.

According to an embodiment of the disclosure, FIG. 1 illustrates a block diagram a system 100 for analyzing a wound in the person or a patient. FIG. 2 shows a schematic architecture of the system 100. It should be appreciated that the system 100 may also be referred as a wound management system 100. In an embodiment, the network 106 may be a wireless or a wired network, or a combination thereof. In an example, the network 106 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 106 may include a variety of network devices, including routers, bridges, servers, computing devices, storage devices. The network devices within the network 106 may interact with the system 100 through communication links.

The system 100 may be implemented in a workstation, a mainframe computer, a server, and a network server. In an embodiment, the computing device 102 further comprises one or more hardware processors 108, one or more memory 110, hereinafter referred as a memory 110 and a data repository 112, for example, a repository 112. The memory 110 is in communication with the one or more hardware processors 108, wherein the one or more hardware processors 108 are configured to execute programmed instructions stored in the memory 110, to perform various functions as explained in the later part of the disclosure. The repository 112 may store data processed, received, and generated by the system 100. The memory 110 further comprises a plurality of modules for performing various functions. The plurality of modules comprises a training module 114, an image segmentation module 116, an AI based estimation module 118, and a self-learning module 120 as shown in the block diagram of FIG. 1.

The system 100 supports various connectivity options such as BLUETOOTH®, USB, ZigBee and other cellular services. The network environment enables connection of various components of the system 100 using any communication link including Internet, WAN, MAN, and so on. In an exemplary embodiment, the system 100 is implemented to operate as a stand-alone device. In another embodiment, the system 100 may be implemented to work as a loosely coupled device to a smart computing environment. The components and functionalities of the system 100 are described further in detail.

An example of a software block diagram 300 of the system 100 is shown in the FIG. In general, the system 100 comprises a patient portal 302, a physician portal 304 and a server 306 or any other place where wound analysis happens. 3. In an example, the patient portal 302 is an application present in the mobile phone of the patient, where the patient can click an image of a wound to be analyzed and share it to the server for wound analysis. Normally, the patient portal 302 comprises following features: a camera for capturing the image to be analyzed, an interface through which patient ID, date and time stamp can be entered, converting image to byte string array, ability to upload json to server, camera calibration and a display screen displaying a healing index as feedback from the analysis. In an embodiment the date and time stamp can be taken automatically from the processor.

According to an embodiment of the disclosure, the system 100 is also configured to a plurality of patient parameters as input to the physician analyzing the image via the patient portal 302, wherein the plurality of patient parameters comprises patient name, ID, patient medical history, and patient physical statistics.

Figure 3:
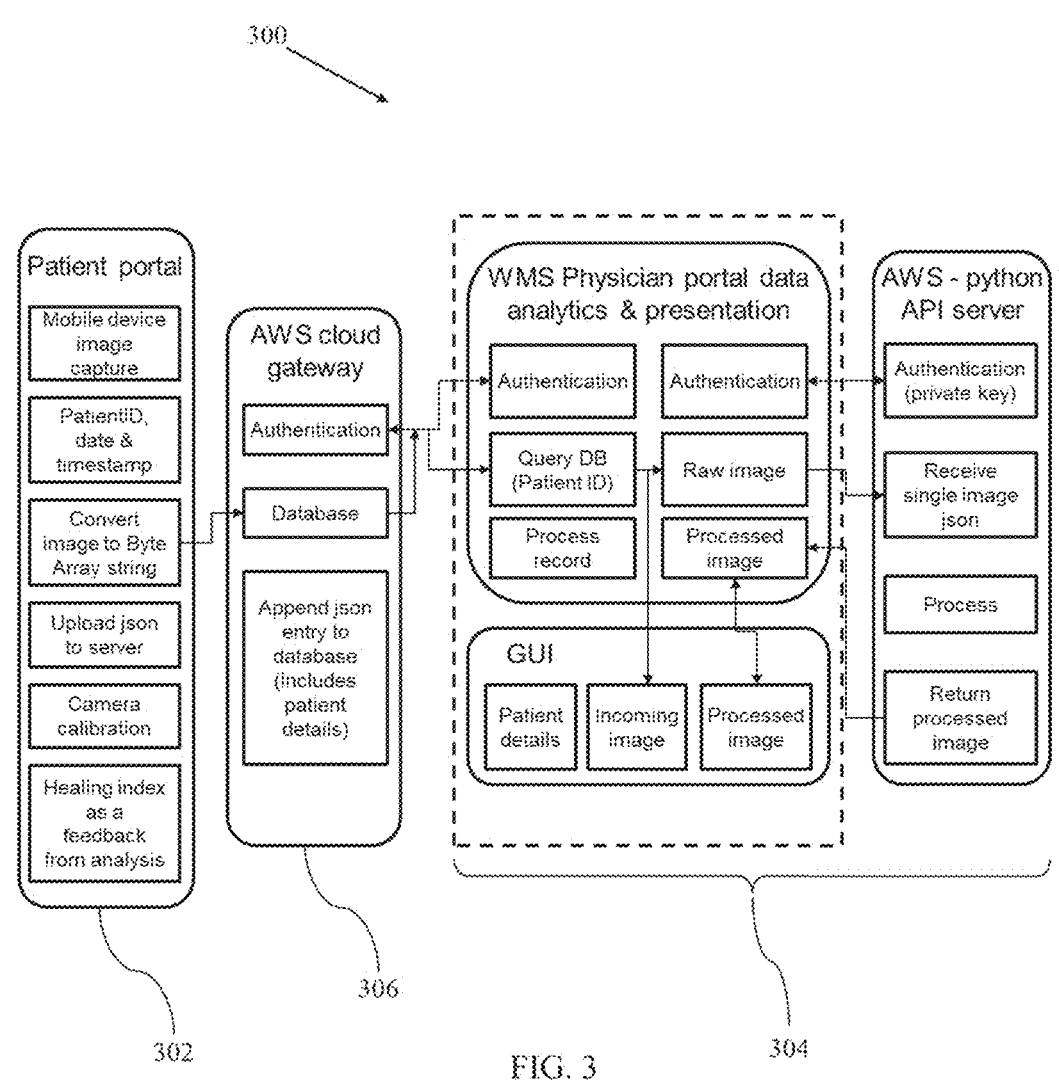
FIG. 3 is an example of a software block diagram of the system of FIG. 1 according to some embodiments of the present disclosure.

FIG. 3 also shows the server such as Amazon web service (AWS) cloud gateway, the server 306 comprises authentication, database and feature for appending json to database. The physician portal 304 comprises a GUI showing patient details, input image and the analyzed image. In an example the physician portal is in communication with an AWS-Python API Server.

According to an embodiments of the disclosure, the user interface 104 is configured to receive a plurality of images. The plurality of images is further used for training a deep learning mode using the training module 114.

Figure 4:
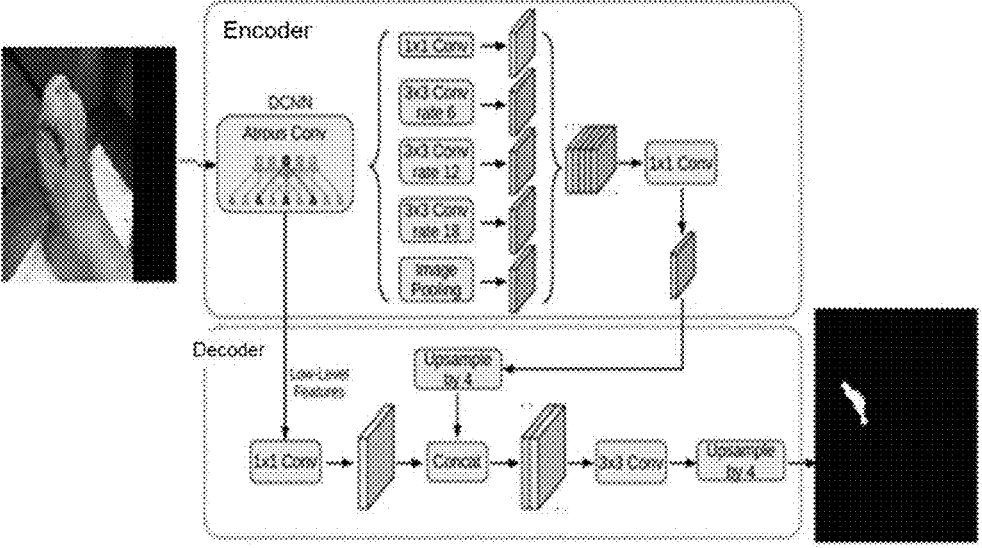
FIG. 4 shows an architecture of a DeepLabV3+ model according to some embodiments of the present disclosure.

According to an embodiment of the disclosure, the system 100 comprises the training module 114. The training module 114 is configured to train a deep learning (DL) model using the plurality of preprocessed images, wherein the deep learning model having an encoder decoder architecture as shown in FIG. 4. the encoder decoder architecture comprises: a pre-trained Resnet50 as the encoder, an Atrous spatial pyramid pooling (ASPP) comprising of dilated convolution, wherein the ASPP is connected to the encoder, a bilinear up sampler configured to up sample the plurality of images by a factor of four, and a channel wise attention mechanism using squeeze and excitation (SE) network, designed to improve representational power of the network by enabling to perform dynamic channel-wise feature recalibration.

To make the training more efficient, transfer learning was used for the deep learning model. Instead of randomly initializing the weights, the Resnet50 model, pre-trained on the Image Net dataset is loaded before the model is trained on the plurality of data. Transfer learning with the pre-trained model is beneficial to the training process in the sense that the weights converge faster and better.

In an embodiment, DeepLabV3+ architecture was used. This is an encoder decoder architecture with Atrous Spatial Pyramid Pooling (ASPP) and bi-linear up sampling. The network begins with a pre-trained Resnet50 as encoder, which is followed by ASPP. The ASPP consists of dilated convolution which helps to encode multi-scale contextual information. It is followed by a bilinear up sampling by a factor of 4 to get the output mask. A novel Channel wise Attention Mechanism was also utilized which is using— Squeeze and Excitation (SE) Network, an architectural unit designed to improve the representational power of a network by enabling it to perform dynamic channel-wise feature recalibration.

Atrous Spatial Pyramid Pooling (ASPP) is a semantic segmentation module for resampling a given feature layer at multiple rates prior to convolution. This amounts to probing the original image with multiple filters that have complementary effective fields of view, thus capturing objects as well as useful image context at multiple scales. Rather than resampling features, the mapping is implemented using multiple parallel Atrous convolutional layers with different sampling rates.

Squeeze and Excitation Networks Architecture consists of three operations: Squeeze, Excitation, and Scaling. The squeeze operation is mainly used to extract the global information from each channel of the feature map. The feature map is basically the output of the convolution layer, which is a 4D tensor of size $B \times H \times W \times C$. In the Squeeze operation the Global Average Pooling (GAP) is used to reduce the $B \times H \times W \times C$ feature map to $B \times 1 \times 1 \times C$ since GAP was performing much better than Global Max Pooling (GMP). Since the feature map is now reduced to a smaller dimension ($B \times 1 \times 1 \times C$), basically for each channel of size $H \times W$ is reduced to a singular vector. For the excitation operation, a fully connected multi-Layer perceptron (MLP) with a bottleneck structure is used. The MLP is used to generate the weights to scale each channel of the feature map adaptively.

The excitation operation passes the "excited" tensor of shape B×1×1×C. This tensor is then passed through a sigmoid activation function. The sigmoid activation function converts the tensor values in the range of 0 and 1. Then an element-wise multiplication is performed between the output of the sigmoid activation function and the input feature map. If the value is close to 0 means the channel is less important so, the values of the feature channel would be reduced, and if the value is close to 1, this means that is channel is important.

Thus, the Squeeze and Excitation Network basically scale each channel information. It reduces the non-relevant channel information and the relevant channel are not much affected. So, after the whole operation, the feature map only contains the relevant information, which increases the representational power of the entire network.

According to an embodiment of the disclosure, the system 100 comprises the image segmentation module 116. The image segmentation module 116 configured to preprocess an input image of the wound to be analyzed; generate an output image from the preprocessed image using the trained deep learning model; and post-process the output image using a binary segmentation mask with a fixed threshold of a predefined number. The binary segmentation masks predicted by the trained DL model are grayscale images with pixel intensities that range from 0 to 255. In the post processing step, binary segmentation masks are first generated from thresholding with a fixed threshold of 127, which is half the max intensity.

According to an embodiment of the disclosure, the system 100 comprises the AI based estimation module 118. The AI based estimation module 118 configured to perform morphology operations on the segmented image to remove the small regions and spurious noises to fill the small holes within the wound to improve a true positive rate; perform connected component analysis on the binary image to label connected regions; calculate a plurality of wound parameters of the wound by measuring the labelled connected regions; and overlay the calculated plurality of parameters and wound segmented boundary on the image of the wound.

Figure 5:
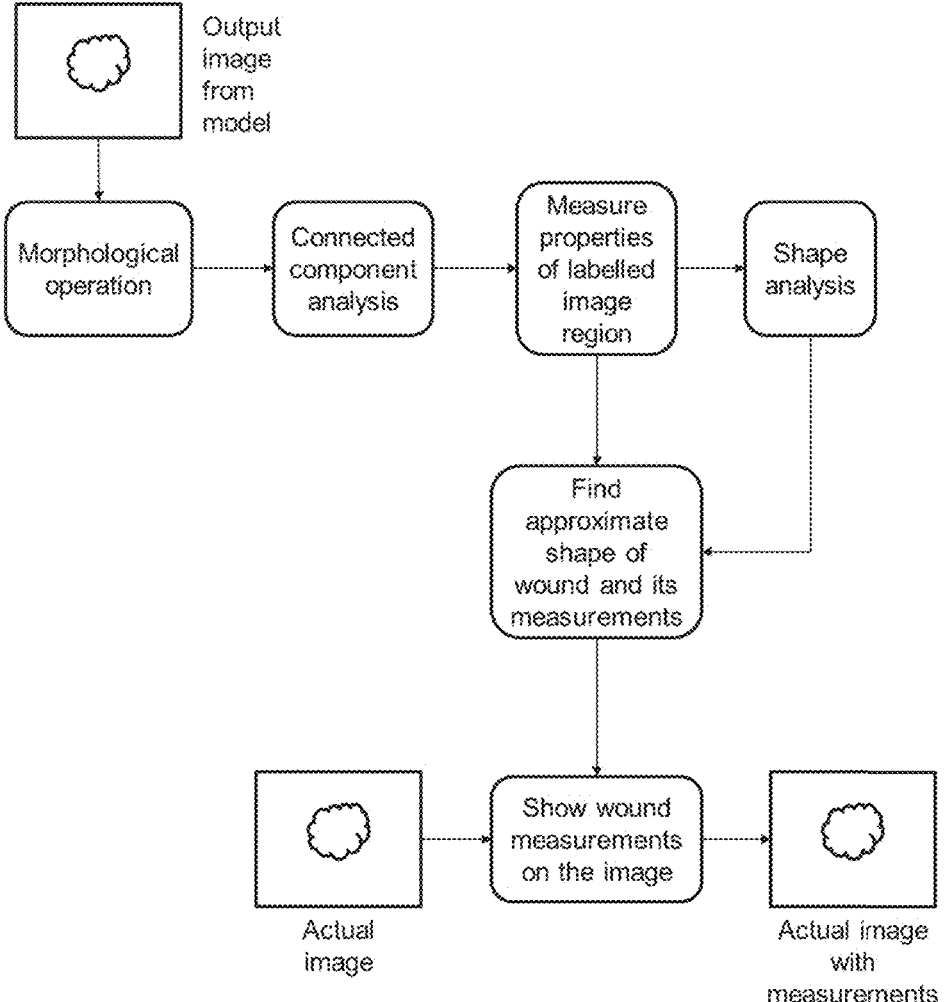
FIG. 5 shows a block diagram of an AI based estimation module according to some embodiments of the present disclosure.

The block diagram of the AI based estimation module 118 is shown in FIG. 5, which includes morphological operations, connected component analysis, and shape analysis followed by wound measurements. Input to the post processing stage is the binary segmentation mask that is generated from the deep learning output by thresholding. Morphology operations are performed on the binary mask to remove the small regions/spurious noises and to fill the small holes within the wound to improve the true positive rate. Sometimes, the blood stain could be identified as wound by the deep learning network causing small false-positive region/noise in the segmented mask. This small false-positive region is detected and removed by finding small, connected components in the segmented mask. On the other hand, the abnormal tissue like fibrinous tissue inside the wound could be treated as non-wound by the network representing it as small holes inside the segmented mask. These holes are detected and filled by finding the small, connected components.

Connected component analysis is used to label the connected regions followed by measurement of those labeled connected regions. The measurements, such as, area, perimeter, circle diameter, major and minor axis length of ellipse etc. are used in conjunction with shape analysis to find the approximate shape of the wound and its measurements. Finally, the measured wound parameters and wound segmented boundary are overlaid on the wound image.

According to an embodiment of the disclosure, the system 100 also comprises the self-learning module. The self-learning module configured to receive annotating on the output image of the wound provided by a user, if the segmented output image is not matching with the input image based on an evaluation done by the user; and utilizing the annotation provided by the user to self-learn the training module to improve the accuracy of the system. In another embodiment, the user can provide an annotation tool that has been developed based on graph-cut method with minimum touch points of two or more that distinguish the foreground and background of the image. In yet another embodiment, the user can provide the annotation tool using a manual re-draw approach.

Figure 6A:
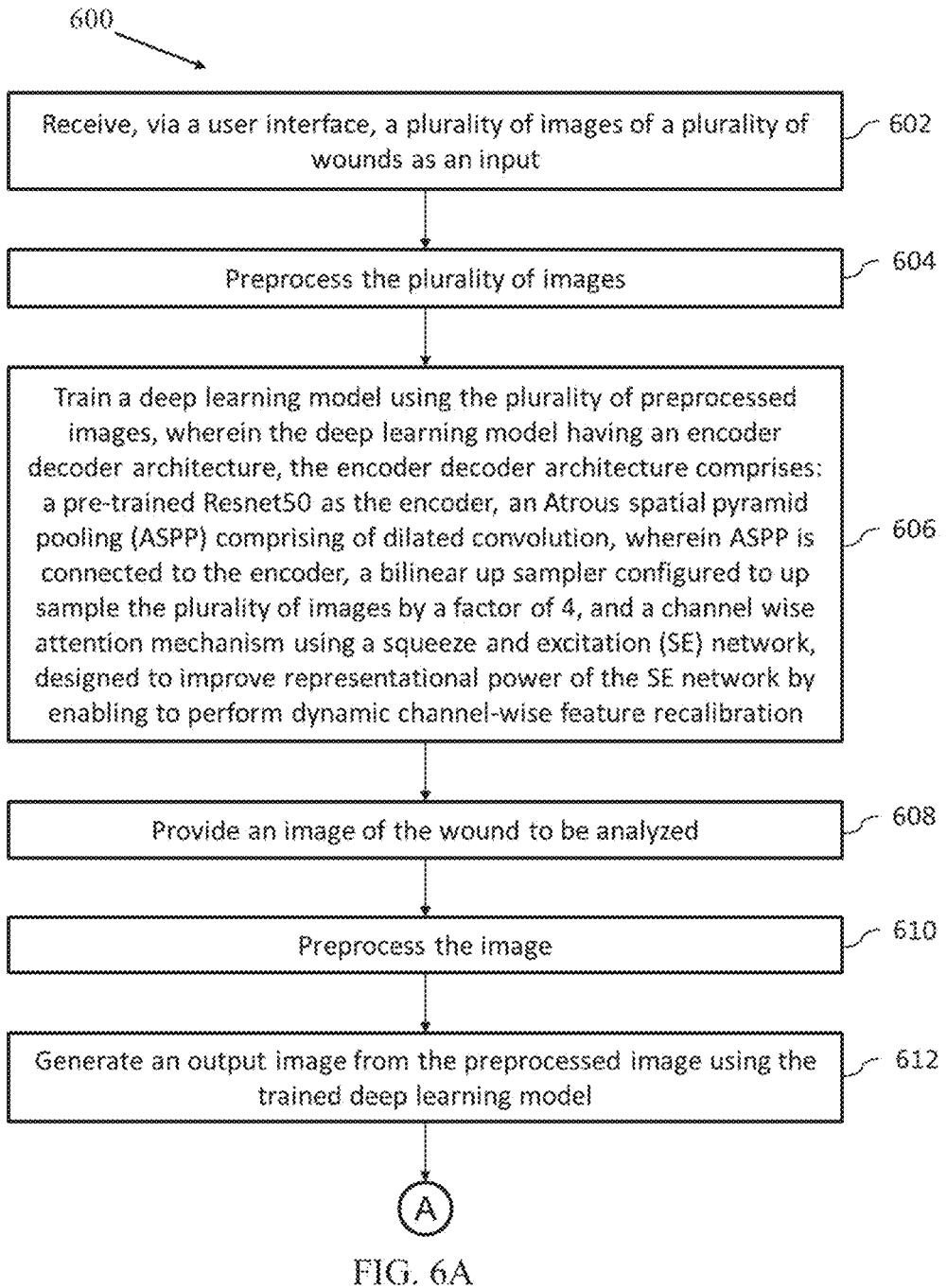
FIG. 6A-6B is a flowchart of an artificial intelligence (AI) based method for analyzing a wound according to some embodiments of the present disclosure.
Figure 6B:
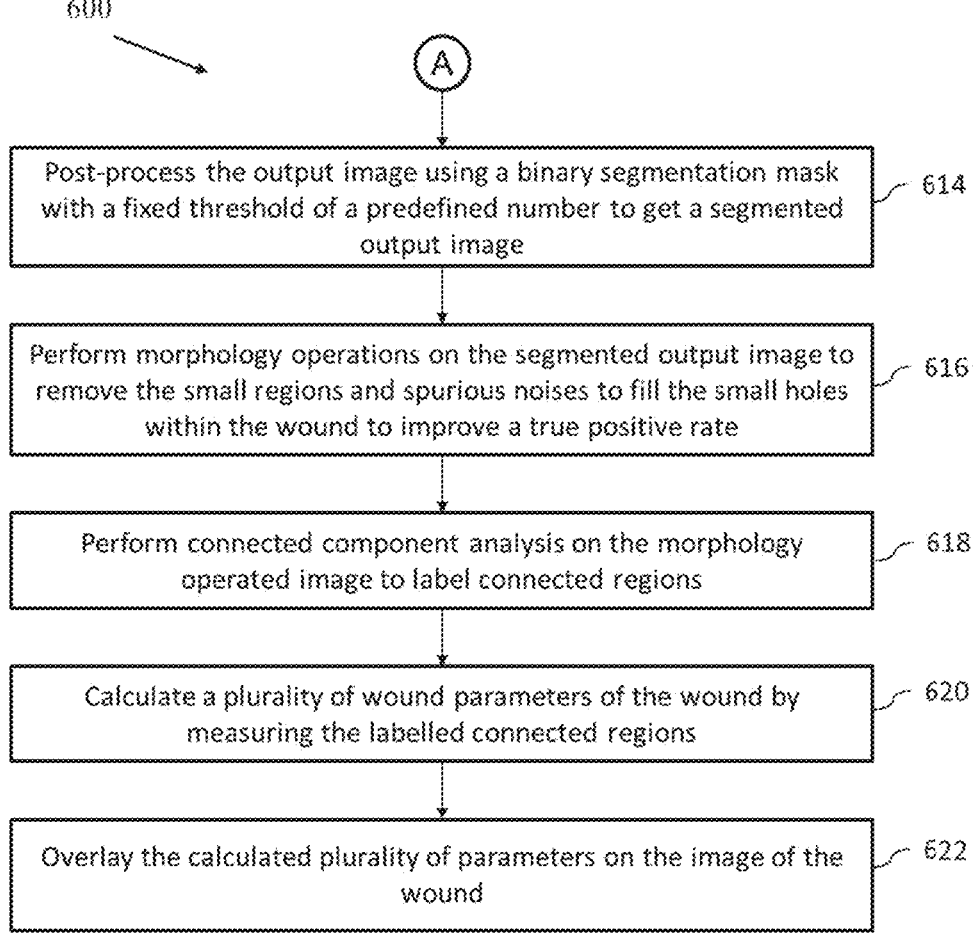

FIG. 6A-6B illustrates a flow chart of an AI based method 600 for analyzing the wound in the person, in accordance with an example embodiment of the present disclosure. The method 600 depicted in the flow chart may be executed by a system, for example, the system 100 of FIG. 1. In an example embodiment, the system 100 may be embodied in the computing device.

Operations of the flowchart, and combinations of operations in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 600 are described with help of system 100. However, the operations of the method 600 can be described and/or practiced by using any other system.

Initially at step 602 of the method 600, the plurality of images of a plurality of wounds is received as the input via the user interface 104. At step 604, the plurality of images is then preprocessed. Further at step 606, the deep learning model is trained using the plurality of preprocessed images, wherein the deep learning model having an encoder decoder architecture, the encoder decoder architecture comprises: a pre-trained Resnet50 as the encoder, an Atrous spatial pyramid pooling (ASPP) comprising of dilated convolution, wherein the ASPP is connected to the encoder, a bilinear up sampler configured to up sample the plurality of images by a factor of four, and a channel wise attention mechanism using a squeeze and excitation (SE) network, designed to improve representational power of the SE network by enabling to perform dynamic channel-wise feature recalibration.

At step 608 of the method 600, the image of the wound to be analyzed is provided. At step 610, the image to be analyzed is preprocessed. In the next step 612, the output image is generated from the preprocessed image using the trained deep learning model. Further at step 614, the output image is preprocessed using the binary segmentation mask with the fixed threshold of the predefined number to get the segmented output image.

In the next step 616 of the method 600, morphology operations are performed on the segmented output image to remove the small regions and spurious noises to fill the small holes within the wound to improve a true positive rate. In the next step 618, connected component analysis is performed on the morphology operated image to label connected regions. Further at step 620, the plurality of wound parameters of the wound is calculated by measuring the labelled connected regions. And finally, at step 622, the calculated plurality of wound parameters and wound segmented boundary is overlaid on the image of the wound. This overlaid image can be displayed on the display screen which can further be analyzed by the physician.

According to an embodiment of the disclosure, the method 100 further comprises receiving annotation on the segmented output image of the wound provided by a user, if the segmented output image is not matching with the input image based on an evaluation done by the user; and utilizing the annotation provided by the user to self-learn the training module 114 to improve the accuracy of the system 100.

According to an embodiment of the disclosure, the system 100 also comprises a 3D printer. The 3D printer is configured to provide a wound dress patch estimated using the plurality of wound parameter.

According to an embodiment of the disclosure, the system 100 can also be explained with the help of experimental results. In an example, preexisting wound care data have been merged segmentation dataset, which leads to 2119 images. Further, images were resized and augmented as a process homogeneousness, extending the dataset as 10937 images. The DeepLab V3+, and Resnet-50 encoder was adapted with pre-trained weights from image net dataset, resulting in a dice score of 0.9206 and IOU −0.85.

Later the performance was improved to a dice score of 0.926 and IOU-0.86 for DeepLab-V3+ with squeeze & Excite model. Further, the AI module is implemented with morphological operations, connected component analysis, and shape analysis, improving accuracy and providing the wound parameter and metrics such as area, perimeter, circle diameter, major and minor axis length of an ellipse. In addendum, to ease the wound care Pro with the mobile app, a lightweight approach was attempted using the U-Net model with Mobile Net Encoder, which yields a dice score of 0.91 and IOU of 0.83.

For homogeneousness, the images were resized to 256*256 and the Image Augmentation techniques which includes, Gamma, Saturation, Hue, Horizontal and Vertical Flips etc. were adapted, which made the training data set as 10746 wound images. The augmentations were not applied to the testing and validation sets and contained 191 images in each set.

Deep Learning Results and Performance Metrics

The deep learning model in the presented work was implemented in python with Keras and TensorFlow backend. The model was trained on Tesla P100 GPU with 16 GB memory. For updating the parameters in the network, the Adam optimization algorithm was employed. Dice loss was used as the loss function and also Precision, Recall and the Dice score were monitored as the evaluation matrices. The initial learning rate was set to 0.0001 and each minibatch contained 16 images for balancing the training accuracy and efficiency. A drop out of 0.1 was specified in order to prevent any overfitting. Early stopping was used to terminate the training so that the best result was saved when there was no improvement for more than 10 epochs in terms of validation loss. Eventually, the deep learning model was trained for around 30 epochs before overfitting illustrates the training and validation losses.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem related to accurate, timely and cost effective analysis of the wounds of the person. The embodiment thus provides an AI based method and a system for analyzing the wounds.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs or GPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A system for analyzing a wound, the system comprising:

a user interface for receiving a plurality of images of a plurality of wounds as an input, one or more hardware processors; and a memory in communication with the one or more hardware processors, wherein the one or more first hardware processors are configured to execute programmed instructions stored the memory, the memory further comprises:

a training module configured to train a deep learning model using the plurality of preprocessed images, wherein the deep learning model having an encoder decoder architecture, the encoder decoder architecture comprises:

a pre-trained Resnet50 as the encoder, wherein the pre-trained Resnet50 is loaded with Image Net dataset before training using transfer learning techniques;

an Atrous spatial pyramid pooling (ASPP) comprising of dilated convolution, wherein the ASPP is connected to the encoder, wherein the ASPP is a semantic segmentation module for resampling a feature layer at multiple rates prior to convolution and performs mapping using parallel Atrous convolution layers with different sampling rates and probe original image with multiple filters having complementary effective fields of view;

a bilinear up sampler configured to up sample the plurality of images by a factor of four, and a channel wise attention mechanism using squeeze and excitation (SE) network, designed to improve representational power of the network by enabling to perform dynamic channel-wise feature recalibration and reduce non-relevant channel information, wherein the squeeze and excitation (SE) network consists of three operations including a squeeze operation, an excitation operation and a scaling operation, wherein the squeeze operation extracts global information from each channel of a feature map, wherein the feature map is an output of a convolution layer which is a 4D tensor, wherein the feature map is reduced to a singular vector of a smaller dimension by performing a Global Average Pooling (GAP), wherein a fully connected multi-Layer perceptron (MLP) with a bottleneck structure performs the excitation operation and the MLP generates the weights to scale each channel of the feature map adaptively, wherein the excitation operation passes an excited tensor through a sigmoid activation function which converts tensor values in the range of 0 and 1 and an element-wise multiplication is performed between an output of the sigmoid activation function and the feature map;

an image segmentation module configured to:

preprocess an input image of the wound to be analyzed;

generate an output image from preprocessed image using the trained deep learning model; and post-process the output image using a binary segmentation mask with a fixed threshold of a pre-defined number;

an AI based estimation module configured to:

perform morphology operations on the segmented image to remove small regions and spurious noises to fill small holes within the wound to improve a true positive rate;

perform connected component analysis on the binary image to label connected regions;

calculate a plurality of wound parameters of the wound by measuring the labelled connected regions; and overlay the calculated plurality of wound parameters on the image of the wound.

2. The system of claim 1 further comprises a self-learning module, wherein the self-learning module configured to:

receive annotating on the output image of the wound provided by a user, if the segmented output image is not matching with the input image based on an evaluation done by the user; and utilizing the annotation provided by the user to self-learn the training module to improve the accuracy of the system.

3. The system of claim 1 further comprises a 3D printer configured to provide a wound dress patch estimated using the plurality of wound parameter.

4. A processor implemented method for analyzing a wound, the method comprising:

receiving, via a user interface, a plurality of images of a plurality of wounds as an input;

preprocessing, via one or more hardware processors, the plurality of images;

training, via the one or more hardware processors, a deep learning model using the plurality of preprocessed images, wherein the deep learning model having an encoder decoder architecture, the encoder decoder architecture comprises:

a pre-trained Resnet50 as the encoder, wherein the pre-trained Resnet50 is loaded with Image Net dataset before training using transfer learning techniques;

an Atrous spatial pyramid pooling (ASPP) comprising of dilated convolution, wherein the ASPP is connected to the encoder, wherein the ASPP is a semantic segmentation module for resampling a given feature layer at multiple rates prior to convolution and performs mapping using parallel Atrous convolution layers with different sampling rates and probe original image with multiple filters having complementary effective fields of view:

a bilinear up sampler configured to up sample the plurality of images by a factor of four, and a channel wise attention mechanism using a squeeze and excitation (SE) network, designed to improve representational power of the SE network by enabling to perform dynamic channel-wise feature recalibration and reduce non-relevant channel information, wherein the squeeze and excitation (SE) network consists of three operations including a squeeze operation, an excitation operation and a scaling operation, wherein the squeeze operation extracts global information from each channel of a feature map, wherein the feature map is an output of a convolution layer which is a 4D tensor, wherein the feature map is reduced to a singular vector of a smaller dimension by performing a Global Average Pooling (GAP), wherein a fully connected multi-Layer perceptron (MLP) with a bottleneck structure performs the excitation operation and the MLP generates the weights to scale each channel of the feature map adaptively, wherein the excitation operation passes an excited tensor through a sigmoid activation function which converts tensor values in the range of 0 and 1 and an element-wise multiplication is performed between an output of the sigmoid activation function and the feature map;

providing, via the one or more hardware processors, an image of the wound to be analyzed;

preprocessing, via the one or more hardware processors, the image;

generating, via the one or more hardware processors, an output image from preprocessed image using the trained deep learning model;

post-processing, via the one or more hardware processors, the output image using a binary segmentation mask with a fixed threshold of a predefined number to get a segmented output image;

performing, via the one or more hardware processors, morphology operations on the segmented output image to remove small regions and spurious noises to fill small holes within the wound to improve a true positive rate;

performing, via the one or more hardware processors, connected component analysis on the morphology operated image to label connected regions;

calculating, via the one or more hardware processors, a plurality of wound parameters of the wound by measuring the labelled connected regions; and overlaying, via the one or more hardware processors, the calculated plurality of wound parameters on the image of the wound.

5. The processor implemented method of claim 4 further comprising:

receiving annotation on the segmented output image of the wound provided by a user, if the segmented output image is not matching with the input image based on an evaluation done by the user; and utilizing the annotation provided by the user to self-learn the training module to improve the accuracy of the system.

6. The processor implemented method of claim 4, further comprising displaying a healing index of the analyzed wound to the person, wherein the healing index is estimated based on an area of wound history.

7. The processor implemented method of claim 4 wherein the plurality of wound parameters comprises an area, a perimeter, a circle diameter, a major and a minor axis length of an ellipse, wherein the plurality of wound parameters are used in conjunction with a shape analysis to find approximate shape of the wound and its measurements.

8. The processor implemented method of claim 4, wherein preprocessing comprises image resizing and image augmenting.

9. The processor implemented method of claim 4, wherein the binary segmentation mask is grayscale image with pixel intensities ranging from 0 to 255, wherein the binary segmentation mask is generated from thresholding with a fixed threshold of 127 during the post processing.

10. The processor implemented method of claim 4, wherein the ASPP is configured to encode multi-scale contextual information from the plurality of images.

11. The processor implemented method of claim 4 further comprising a plurality of patient parameters as input to a physician analyzing the image, wherein the plurality of patient parameters comprises patient name, ID, patient medical history, and patient physical statistics.

12. The processor implemented method of claim 4 further comprising integrating with a 3D printer to provide a wound dress patch estimated using the plurality of wound parameter.

13. One or more non-transitory machine-readable information storage mediums comprising one or more instructions which when executed by one or more hardware processors cause;

receiving a plurality of images of a plurality of wounds as an input;

preprocessing the plurality of images;

training a deep learning model using the plurality of preprocessed images, wherein the deep learning model having an encoder decoder architecture, the encoder decoder architecture comprises:

a pre-trained Resnet50 as the encoder, wherein the pre-trained Resnet 50 is loaded with Image Net dataset before training using transfer learning techniques;

an Atrous spatial pyramid pooling (ASPP) comprising of dilated convolution, wherein the ASPP is connected to the encoder, wherein the ASPP is a semantic segmentation module for resampling a given feature layer at multiple rates prior to convolution and performs mapping using parallel Atrous convolution layers with different sampling rates and probe original image with multiple filters having complementary effective fields of view;

a bilinear up sampler configured to up sample the plurality of images by a factor of four, and a channel wise attention mechanism using a squeeze and excitation (SE) network, designed to improve representational power of the SE network by enabling to perform dynamic channel-wise feature recalibration and reduce non-relevant channel information, wherein the squeeze and excitation (SE) network consists of three operations including a squeeze operation, an excitation operation and a scaling operation, wherein the squeeze operation extracts global information from each channel of a feature map, wherein the feature map is an output of a convolution layer which is a 4D tensor, wherein the feature map is reduced to a singular vector of a smaller dimension by performing a Global Average Pooling (GAP), wherein a fully connected multi-Layer perceptron (MLP) with a bottleneck structure performs the excitation operation and the MLP generates the weights to scale each channel of the feature map adaptively, wherein the excitation operation passes an excited tensor through a sigmoid activation function which converts tensor values in the range of 0 and 1 and an element-wise multiplication is performed between an output of the sigmoid activation function and the feature map;

providing an image of the wound to be analyzed;

preprocessing the image;

generating an output image from preprocessed image using the trained deep learning model;

post-processing the output image using a binary segmentation mask with a fixed threshold of a predefined number to get a segmented output image;

performing, via the one or more hardware processors, morphology operations on the segmented output image to remove small regions and spurious noises to fill small holes within the wound to improve a true positive rate;

performing, via the one or more hardware processors, connected component analysis on the morphology operated image to label connected regions;

calculating, via the one or more hardware processors, a plurality of wound parameters of the wound by measuring the labelled connected regions; and overlaying, via the one or more hardware processors, the calculated plurality of wound parameters on the image of the wound.

14. The one or more non-transitory machine readable information storage mediums of claim 13, further comprising:

receiving annotation on the segmented output image of the wound provided by a user, if the segmented output image is not matching with the input image based on an evaluation done by the user; and utilizing the annotation provided by the user to self-learn the training module to improve the accuracy of the system.

15. The one or more non-transitory machine readable information storage mediums of claim 13, further comprising displaying a healing index of the analyzed wound to the person, wherein the healing index is estimated based on an area of wound history.

16. The one or more non-transitory machine readable information storage mediums of claim 13, wherein the plurality of wound parameters comprises an area, a perimeter, a circle diameter, a major and a minor axis length of an ellipse, wherein the plurality of wound parameters are used in conjunction with a shape analysis to find approximate shape of the wound and its measurements.

17. The one or more non-transitory machine readable information storage mediums of claim 13, wherein preprocessing comprises image resizing and image augmenting.

18. The one or more non-transitory machine readable information storage mediums of claim 13, wherein the binary segmentation mask is grayscale image with pixel intensities ranging from 0 to 255, wherein the binary segmentation mask is generated from thresholding with a fixed threshold of 127 during the post processing.

19. The one or more non-transitory machine readable information storage mediums of claim 13, wherein the ASPP is configured to encode multi-scale contextual information from the plurality of images.

20. The one or more non-transitory machine readable information storage mediums of claim 13, further comprising a plurality of patient parameters as input to a physician analyzing the image, wherein the plurality of patient parameters comprises patient name, ID, patient medical history, and patient physical statistics.

* * * * *